(12) United States Patent
Kalergis Parra et al.

(10) Patent No.: US 12,195,523 B2
(45) Date of Patent: Jan. 14, 2025

(54) MONOCLONAL ANTIBODY OR ANTIGEN BINDING FRAGMENT THEREOF THAT BINDS TO THE L PROTEIN OF THE HUMAN PARAINFLUENZA VIRUS (PIV); METHOD AND KIT FOR DETECTING PIV

(71) Applicant: PONTIFICIA UNIVERSIDAD CATOLICA DE CHILE, Santiago (CL)

(72) Inventors: Alexis Mikes Kalergis Parra, Santiago (CL); Susan Marcela Bueno Ramirez, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 874 days.

(21) Appl. No.: 17/418,617

(22) PCT Filed: Dec. 27, 2019

(86) PCT No.: PCT/CL2019/050157
§ 371 (c)(1),
(2) Date: Jun. 25, 2021

(87) PCT Pub. No.: WO2020/132774
PCT Pub. Date: Jul. 2, 2020

(65) Prior Publication Data
US 2022/0089697 A1    Mar. 24, 2022

(30) Foreign Application Priority Data

Dec. 28, 2018  (CL) .................................. 3869-2018

(51) Int. Cl.
*C07K 16/10*     (2006.01)
*G01N 33/569*    (2006.01)

(52) U.S. Cl.
CPC ... *C07K 16/1027* (2013.01); *G01N 33/56983* (2013.01); *C07K 2317/565* (2013.01); *G01N 2333/115* (2013.01); *G01N 2469/10* (2013.01)

(58) Field of Classification Search
CPC .......... C07K 16/1027; C07K 2317/565; G01N 33/56983; G01N 2333/115; G01N 2469/10
See application file for complete search history.

(56) References Cited

U.S. PATENT DOCUMENTS

| 6,015,664 A | 1/2000 | Henrickson et al. |
| 2010/0278813 A1 | 11/2010 | Young et al. |
| 2011/0076268 A1 | 3/2011 | Williamson et al. |
| 2013/0177573 A1 | 7/2013 | Williamson et al. |

FOREIGN PATENT DOCUMENTS

| AU | 2003256823 B9 | 1/2009 |
| CN | 102140550 A | 8/2011 |
| CN | 105441589 A | 3/2016 |
| WO | 2004010935 A3 | 2/2004 |
| WO | 2013112720 A1 | 8/2013 |
| WO | 2017021815 A | 2/2017 |

OTHER PUBLICATIONS

Machiko Nishio, et al., "Human Parainfluenza Virus Type 2 L Protein Regions Required for Interaction With Other Viral Proteins and mRNA Capping", Journal of Virology, vol. 85, No. 2, pp. 725-732, 2011.

Machiko Nishio, et al., "Mapping of Domains on the Human Parainfluenza Type 2 Virus P and NP Proteins That Are Involved in the Interaction With the L Protein", Virology, vol. 273, pp. 241-247, 2000.

Susan E. Stark, et al., "Antibodies That Are Specific for a Single Amino Acid Interchange in a Protein Epitope Use Structurally Distinct Variable Regions", J. Exp. Med., vol. 174, pp. 613-624, 1991.

Joseph L. Waner, et al., "Production of Monoclonal Antibodies Against Parainfluenza 3 Virus and Their Use in Diagnosis by Immunofluorescence", Journal of Clinical Microbiology, vol. 22, No. 4, pp. 535-538, 1985.

J.C. Hierholzer, et al., "Comparison of Monoclonal Antibody Time-Resolved Fluoroimmunoassay With Monoclonal Antibody Capture-Biotinylated Detector Enzyme Immunoassay Virus Antigen Detection", Journal of Clinical Microbiology, vol. 27, No. 6, pp. 1243-1249, 1989.

Satoko Matsunage, et al., "Wheat Germ Cell-Free System-Based Production of Hemagglutinin-Neuraminidase Glycoprotein of Human Parainfluenza Virus Type 3 For Generation and Characterization of Monoclonal Antibody", Frontiers in Microbiology, vol. 5, pp. 1-12, 2014.

Angela R. Branche, MD, et al., Parainfluenza Virus Infection, Seminars in Respiratory and Critical Care Medicine, vol. 37, pp. 538-554, 2016.

International Search Report for Corresponding International Application No. PCT/CL2019/050157 dated Apr. 8, 2020 and English translation.

*Primary Examiner* — Nicole Kinsey White
*Assistant Examiner* — Samadhan Jaising Jadhao
(74) *Attorney, Agent, or Firm* — LUCAS & MERCANTI, LLP

(57) ABSTRACT

Generation of monoclonal antibodies, or fragments thereof, that recognize the human parainfluenza virus (human PIV) chimeric protein L, where the monoclonal antibodies or fragments thereof have a heavy chain variable region and a light chain variable region. In addition, a method of diagnosing human PIV infection in a biological sample of nasopharyngeal secretion is provided, using the monoclonal antibodies in diagnostic kit format.

9 Claims, 6 Drawing Sheets
Specification includes a Sequence Listing.

ID NO: 1, its CDR2 (CDR_{LC2}) is defined by SEQ ID NO: 2 and its CDR3 (CDR_{LC3}) corresponds to SEQ ID NO: 3, and a heavy chain variable region where its CDR1 (CDR_{HC1}) is -->

MONOCLONAL ANTIBODY OR ANTIGEN BINDING FRAGMENT THEREOF THAT BINDS TO THE L PROTEIN OF THE HUMAN PARAINFLUENZA VIRUS (PIV); METHOD AND KIT FOR DETECTING PIV

CROSS REFERENCE TO RELATED APPLICATION

This Application is a 371 of PCT/CL2019/050157 filed on Dec. 27, 2019, which, in turn, claimed the priority of Chilean Patent Application No. 3869-2018 filed on Dec. 28, 2018, both applications are incorporated herein by reference.

Monoclonal antibodies, or fragments thereof, are disclosed, which recognize the chimera protein L of the human parainfluenza virus (PIV), where said monoclonal antibodies or fragments of these comprise a light chain variable region where their CDR1 (CDR$_{LC1}$) is defined according to SEQ ID NO: 1, its CDR2 (CDR$_{LC2}$) is defined by SEQ ID NO: 2 and its CDR3 (CDR$_{LC3}$) corresponds to SEQ ID NO: 3, and a heavy chain variable region where its CDR1 (CDR$_{HC1}$) is defined according to SEQ ID NO: 4, its CDR2 (CDR$_{HC2}$) is defined by SEQ ID NO: 5 and its CDR3 (CDR$_{HC3}$) corresponds to Gly-Ala-Tyr, or a heavy chain variable region where its CDR1 (CDR$_{LC1}$) is defined according to SEQ ID NO: 7, its CDR2 (CDR$_{LC2}$) is defined by SEQ ID NO: 8 and its CDR3 (CDR$_{LC3}$) corresponds to SEQ ID NO: 9, and a heavy chain variable region where its CDR1 (CDR$_{HC1}$) is defined according to SEQ ID NO: 10, its CDR2 (CDR$_{HC2}$) corresponds to SEQ ID NO: 11 and its CDR3 (CDR$_{HC3}$) corresponds to Gly-Ala-Tyr Where said antibodies can be used as detection and/or capture antibody. Also provided is a method for diagnosing PIV infection in a biological sample using monoclonal antibodies, and a diagnostic kit for detecting PIV, comprising at least one monoclonal antibody against PIV as previously described.

BACKGROUND OF THE INVENTION

Human parainfluenza virus produces an infectious disease of the upper respiratory tract that manifests itself in various clinical conditions ranging from the common cold to pneumonia. Laryngotracheobronchitis is the most serious and frequent clinical manifestation.

This disease is caused by a virus of the paramyxovirus type and is easily transmitted from person to person or through drops or small particles that have been expelled through the cough or sneeze of a sick person, which makes it spread quickly and be part of seasonal epidemics.

In the United States, PIV is one of the leading causes of hospitalization for respiratory diseases in young children, occurring between 2% and 17% of cases, which translates into 250,000 visits to emergency rooms and 700,000 hospitalizations. Among children under 5 years of age, 1.2 children are hospitalized for this cause annually, this rate being higher in those under 6 months[1].

[1] www.ncbi.nlm.nih.gov/pmc/articles/PMC5813689/

PIV has a more variable impact compared to other respiratory viruses, being responsible for 3 to 10% of hospitalizations with bronchiolitis, pneumonia and laryngotracheobronchitis. Like respiratory syncytial virus (RSV), PIV causes serious illness in the first six months of life. PIV infection peaks between 4 and 12 years of age[2].

[2] apps.who.int/iris/bitstream/handle/10665/264249/PMC2486968.pdf?sequence=1&isAllowed=y Infection caused by PIV can be diagnosed by using direct detection methods, that is, by detecting antibodies directly in the sample or by serological tests that make it possible to measure the presence of IgM antibody or the increase in IgG titers. Assays with cell lines are also used for the isolation of PIV in the clinical laboratory.

In the case of virus isolation in cell cultures, this corresponds to a specific and sensitive method, however it has the disadvantage that it takes between 10-15 days to confer a result, being rather a confirmation technique than an initial diagnosis by its slowness. In the case of serological tests that allow to measure the presence of IgM and IgG antibodies in the patient, these are generic tests that do not allow to determine specifically the infection by PIV virus, nor to determine the type of PIV. There are 4 types of PIV, type 1, 2, 3 and 4, being type 1 and 2 the ones that usually appear as epidemic.

Additionally, molecular techniques such as the polymerase chain reaction (PCR) are also used to detect certain RNA segments contained in the virus, from a reverse transcription of the RNA to complementary DNA, using the latter as a template to carry out the PCR. In document U.S. Pat. No. 6,015,664A is filed a method to determine the presence or absence of multiple viral infections in a biological sample by means of a multiplex PCR assay. The method includes nucleotide primers along with probes for the detection of complementary nucleic acid sequences of human parainfluenza virus 1, 2, and 3, respiratory syncytial virus A and B, and influenza virus, A and B.

In document CN102140550A a RT-PCR kit for detecting parainfluenza virus in one step is disclosed, where the kit includes specific primers for parainfluenza virus. A.

For its part, document CN105441589A describes a parainfluenza virus type 1, 2, 3 and 4 detection kit, by means of a quadruple PCR. The quadruple PCR detection kit comprises human parainfluenza virus-specific genetic primers and probes.

There are also various kits based on immunofluorescence for the detection of various respiratory viruses, including parainfluenza. For example, D3 Ultra DFA (direct fluorescent antibody) kit allows the qualitative identification of various respiratory viruses: influenza A, influenza B, respiratory syncytial virus, adenovirus, parainfluenza 1, parainfluenza 2, and parainfluenza 3.

Based on the above-mentioned background, it is essential to generate and have an efficient, rapid and low-cost detection method for the detection of parainfluenza virus that can compete with the diagnostic methods currently used. In this case, the use of monoclonal antibodies that detect proteins present in the virus are considered as an alternative to improve the detection of the influenza virus.

DESCRIPTION OF THE INVENTION

The present invention relates to specific monoclonal antibodies against chimeric protein L or fragments thereof, of the human parainfluenza virus, hereinafter PIV. In particular, the invention corresponds to monoclonal antibodies, or fragments thereof, that recognize the chimera protein L of the human parainfluenza virus (PIV) secreted by hybridomas 2E11B5 and 4D8C6, where said monoclonal antibodies or fragments of these comprise a light chain variable region where their CDR1 (CDR$_{LC1}$) is defined according to SEQ ID NO: 1, its CDR2 (CDR$_{LC2}$) is defined by SEQ ID NO: 2 and its CDR3 (CDR$_{LC3}$) corresponds to SEQ ID NO: 3, and a heavy chain variable region where its CDR1 (CDR$_{HC1}$) is defined according to SEQ ID NO: 4, its CDR2 (CDR$_{HC2}$) is defined by SEQ ID NO: 5 and its CDR3 (CDR$_{HC3}$) corresponds to Gly-Ala-Tyr, or a heavy chain variable region where its CDR1 (CDR$_{LC1}$) is defined according to SEQ ID NO: 7, its CDR2 (CDR$_{LC2}$) is defined by SEQ ID NO: 8 and its CDR3 (CDR$_{LC3}$) corresponds to SEQ ID NO: 9, and a heavy chain variable region where its CDR1 (CDR$_{HC1}$) is defined according to SEQ ID NO: 10, its CDR2 (CDR$_{HC2}$) corresponds to SEQ ID NO: 11 and its CDR3 (CDR$_{HC3}$) corresponds to Gly-Ala-Tyr Said antibodies can be used as detection and/or capture antibody. Also provided is a method for diagnosing PIV infection in a biological sample using monoclonal antibodies, and a diagnostic kit for detecting PIV, comprising at least one monoclonal antibody against PIV as previously described.

Since antigen was not completely conserved, but parts of the sequence were conserved, a new sequence was generated from the union of the conserved parts. Therefore, the antibodies recognize a chimera protein, particularly the chimera protein L of the human parainfluenza virus.

The specific monoclonal antibodies against protein L or fragments thereof present important advantageous and remarkable technical features with respect to other antibodies and methods for detecting viral antigens already existing. First, each virus has specific surface proteins, therefore, other diagnostic techniques based on monoclonal antibodies for other types of respiratory viruses are not comparable to the proposed invention. Detection specificity of antibodies against PIV protein L with respect to other viral antigens, for example against influenza virus PB2 protein, is demonstrated in the results provided in FIGS. 1A and 1B of the present application. From these results it is possible to conclude that the provided antibodies in the scope of the present application only recognize the PIV protein L, and that in ELISA assays with FLU virus antigens no detection signal was observed.

Second, antibodies that are part of the scope of the invention allow specific detection of protein L or fragments thereof, in such a way that they do not compete with each other for the antigen-binding site, nor do they exert an impediment to simultaneously bind to it. Additionally, they allow the detection of protein L or fragments thereof with high sensitivity in samples that contain little antigen amount.

The proposed monoclonal antibodies are capable of detecting protein L, a conserved protein. Strategy for detecting a conserved viral protein allows antibodies that are within the scope of the invention to detect different types of human parainfluenza virus, including parainfluenza 1, 2, 3 and 4.

When reference is made to CDR sequences in the present invention, these correspond to short sequences found in the variable domains of proteins that have antigen detection function. CDR sequences for the heavy chain ($CDR_{HC}$) and light chain ($CDR_{LC}$) of the antibodies secreted by hybridomas 2E11B5 and 4D8C6.

Monoclonal antibodies described can be used for PIV infection determination, diagnosis and/or detection assays. These antibodies can be used simultaneously to increase detection sensitivity of clinical samples where there is little quantity and availability of antigen. In this regard, it is also provided a PIV infection diagnosis method in a biological sample, which comprises contacting the biological sample with the monoclonal antibody against PIV protein L or a fragment thereof according to the claim, and detecting the binding of the antibody with the antigen. Biological sample can be, but is not limited to, infected in vitro cells with PIV, nasal secretions, nasal washes, cerebrospinal fluid, pharyngeal secretions and/or bronchial washes or secretions. As part of the method, the assay used for the detection of antigen-antibody binding is selected from ELISA, luminex, immunofluorescence, immunohistochemistry, immunochromatography, flow cytometry, cell sorter, immunoprecipitation and Western blot.

Present invention also includes a diagnostic kit to detect the human influenza virus, which comprises: a monoclonal antibody against PIV protein L or a fragment thereof, where said antibody can act as a capture or detection antibody, where particularly, the detection antibody is conjugated to a marker for its detection; a solid support to which the antibody is attached; and reagents for detecting the marker included in the detection antibody, such as fluorophores, biotin, radioisotopes, metals, and enzymes.

In the present invention when it refers to capture antibody, this corresponds to the antibody that specifically binds to the antigen. In the case of the detection antibody, this corresponds to the antibody to which a marker is conjugated to be detected by different tests such as immunochromatographic test, luminex, flow cytometry, immunofluorescence, radioimmunoassay, Western blot, Dot blot, ELISA, luminex, immunodiffusion. or immunoprecipitation.

Antibodies that are part of the present invention can act dually as a capture antibody or as a detection antibody when coupled to a detection marker. Detection marker will be conjugated to the detection antibody, and this can correspond, without limitation, to fluorophores, biotin, radioisotopes, metals and enzymes. Preferably, the detection antibody is conjugated to reporter system based on the detection of horseradish peroxidase (HRP) enzyme activity.

BRIEF DESCRIPTION OF THE DRAWINGS

FIG. 1: PIV chimera protein L detection by monoclonal antibodies produced by 2E11B5 and 4D8C6 hybridomas, using an indirect ELISA assay. The plate was activated with 50 ng of purified recombinant PIV protein L, 50 ng of Flu PB2 protein (as a specificity control) and 20 μg of bacterial lysate from no-plasmid *E. coli* BL21 strain (used as specificity control) and 3 clones (C1, C2 and C3) of the same strain, in which protein L was overexpressed. Control wells with no antigen, with primary antibody, with anti-mouse IgG, HRP conjugated (not activated/unactivated) and wells with no antigen or primary antibody, only with anti-mouse IgG (HRP), data not shown in graph. Subsequently, the wells were incubated with the anti-L antibodies from the 2F11B1 hybridoma, in an amount of 170 ng (A) and the 4D8C6 hybridoma in an amount of 170 ng (B). No commercial antibody against protein L was used, since none are currently available that can be used in ELISA technique. Data shown in the graph express detected absorbance at 450 nm, emitted by the conversion of Tetramethylbenzidine substrate to a colored compound, catalyzed by Horseradish peroxidase (HRP)enzyme present in a secondary anti-mouse IgG antibody that specifically bound to the antibodies secreted by the hybridomas 2F11B1 and 4D8C6. Values correspond to the standard deviation in absorbance average +/− emitted by each sample in at least two independent experiments. *$P<0.05$ and **$P<0.01$ by parametric student test comparing the results of PB2-Flu protein versus those of L-PIV, and on the other, one-way ANOVA test was used comparing *E. coli* BL21 lysate with no plasmid versus *E. coli* BL21 lysate that overexpressed protein L. The letters ns mean that no significant difference was observed.

FIG. 2: Sensitivity determination of monoclonal antibodies produced by 2E11135 and 4D8C6 hybridomas in the detection of PIV protein L. ELISA plates were activated with 1:2 serial dilutions, starting with 50 ng of protein L and ending with 0.04 ng. Subsequently, the wells were incubated with the anti-L antibodies from the 2E11B5 hybridoma, in an amount of 170 ng (A) and the 4D8C6 hybridoma in an amount of 170 ng (B). Non-activated wells were included as a negative control. Data shown in the graph express absorbance at 450 nm, emitted by the conversion of Tetramethylbenzidine substrate to a colored compound, catalyzed by Horseradish peroxidase (HRP)enzyme present in anti-L antibodies from the hybridomas 2E11B5 and 4D8C6 in an amount of 170 ng (A and B). Values correspond to the standard deviation in absorbance average +/− emitted by each sample in at least two independent experiments. P<0.01 and *P<0.001 by parametric student test comparing the results of well called control (with no sample) versus each of the dilutions of protein L.

FIG. 4: protein L of PIV detection on infected cells, by monoclonal antibodies produced by 2E11135 and 4D8C6 hybridomas, using an Luminex assay. The plate was activated with 50 ng of purified PIV recombinant protein L, 20 µg of uninfected (used as a specificity control) and PIV-infected MDCK cells. Control well with no antigen, with primary antibody, with HRP-conjugated anti-mouse IgG (NTC) was included. Subsequently, the wells were incubated with the anti-L antibodies from 2E11B5 hybridoma (conjugated to 21 region of PIV), in an amount of 50 microspheres/µl, which was used as capture antibody and 4D8C6 hybridoma at a concentration of 4 µg/mL used as biotin-conjugated detection antibody. Subsequently, the antibodies and sample complex was incubated with Streptavidin/Phycoerythrin at a concentration of 6 µg/mL. Data shown in the graph express the mean fluorescence intensity (MFI). Non-parametric Student's test was performed comparing uninfected cells versus those infected with PIV, and recombinant protein L versus negative control (P<0.01 and **P<0.0001).

FIG. 5: PIV detection in clinical samples by ELISA Sandwich and Luminex Sandwich-type, using the combination of monoclonal antibodies secreted by 2E11135 and 4D8C6 hybridomas for PIV. A) ELISA plates were activated with 170 ng of secreted antibody by 2E11B5 hybridoma (anti-PIV), functioning as capture antibody. Activated wells with capture antibodies for each virus were incubated with 50 µL of nasopharyngeal swab (NPS) samples from patients with viral respiratory symptoms. As negative controls, 10 samples of healthy controls were analyzed. 16 samples of patients PIV-positive were used and as a specificity control, 3 samples of Influenza virus (Flu)-positive patients were included. As a positive control, wells were included to which purified L-PIV protein was added. For the detection of captured protein by 2E11B5 antibody, antibodies produced by 4D8C6 hybridoma, conjugated to the Horseradish Peroxidase enzyme, were used in a 1:2000 dilution (1.8 ng/µL per well). B) Luminex plates were activated with 50 magnetic microspheres per µl, which were conjugated with the secreted antibody by 2E11B5 hybridoma (anti-PIV), functioning as a capture antibody. Conjugated microspheres were incubated with 50 µL of nasopharyngeal swab (NPS) samples from patients with viral respiratory symptoms. As negative controls, 8 samples of healthy controls were analyzed. 14 PIV-positive patient samples were used and wells were included as positive control to which purified L-PIV protein was added. For the detection of captured protein by 2E11B5 antibody, antibodies produced by 4D8C6 hybridoma, conjugated to biotin fluorophore were used at a concentration of 4 µg/mL. The complex (conjugated microspheres with capture antibody, antigen and detection antibody) is incubated with Streptavidin/Phycoerythrin at a concentration of 6 µg/mL. Data shows the median value of emitted absorbance at 450 nm (A) or from MFI (B) of each sample (P<0.01 and **P<0.0001; using the non-parametric student's test comparing PIV-positive patients versus healthy controls, and against the used viruses as a specificity control).

Examples that make it possible to demonstrate the different applications of the monoclonal antibodies of the invention.

Example 1: Determination of the Nucleotide Sequence Encoding the Light (VL) and Heavy (VH) Chains of the Variable Region of Anti-L PIV Antibody Secreted by 2E11B5 Hybridoma 2E11B5 hybridoma was grown in DMEM-high glucose culture medium supplemented with 3.7 g/L of Sodium Bicarbonate and 10% fetal bovine serum, at 37° C. (98.6° F.) with 10% $CO_2$, up to a cell density of 700,000 cells/mL. Total RNA of $3.5 \times 10^6$ cells was obtained, performing a treatment with Trizol compound (Invitrogen). 0.5 µg of RNA was used to generate the cDNA by reverse transcription reaction with the PrimeScript™ 1st Strand cDNA Synthesis kit, which uses isotype-specific universal primers. The antibody heavy and light chain were amplified according to the GenScript rapid amplification of cDNA ends (RACE) standard operating procedure (SOP). Amplified antibody fragments were separately cloned into a standard cloning vector. PCR colony was performed to identify clones which have the correct size inserts. At least five colonies with inserts of the correct size were sequenced for each fragment. Sequences of different clones were aligned and the consensus sequence of these clones was provided. Nucleotide sequences of the heavy and light chains of antibodies secreted by 2E11B5 hybridoma correspond to those identified as SEQ ID NO. 1; SEQ ID NO.2 respectively.

Example 2: Determination of the Nucleotide Sequence Encoding the Light (VL) and Heavy (VH) Chains of the Variable Region of Anti-L PIV Antibody Secreted by 4D8C6 Hybridoma 4D8C6 hybridoma was grown in DMEM-high glucose culture medium supplemented with 3.7 g/L of Sodium Bicarbonate and 10% fetal bovine serum, at 37° C. (98.6° F.) with 10% $CO_2$, up to a cell density of 700,000 cells/mL. Total RNA of $3.5 \times 10^6$ cells was obtained, performing a treatment with Trizol compound (Invitrogen). 0.5 µg of RNA was used to generate the cDNA by reverse transcription reaction with the PrimeScript™ 1st Strand cDNA Synthesis kit, which uses isotype-specific universal primers. The antibody heavy and light chain were amplified according to the GenScript rapid amplification of cDNA ends (RACE) standard operating procedure (SOP). Amplified antibody fragments were separately cloned into a standard cloning vector. PCR colony was performed to identify clones which have the correct size inserts. At least five colonies with inserts of the correct size were sequenced for each fragment. Sequences of different clones were aligned and the consensus sequence of these clones was provided. Nucleotide sequences of the heavy and light chains of antibodies secreted by 4D8C6 hybridoma correspond to those identified as SEQ ID NO. 3; SEQ ID NO. 4 respectively.

Figure 1:
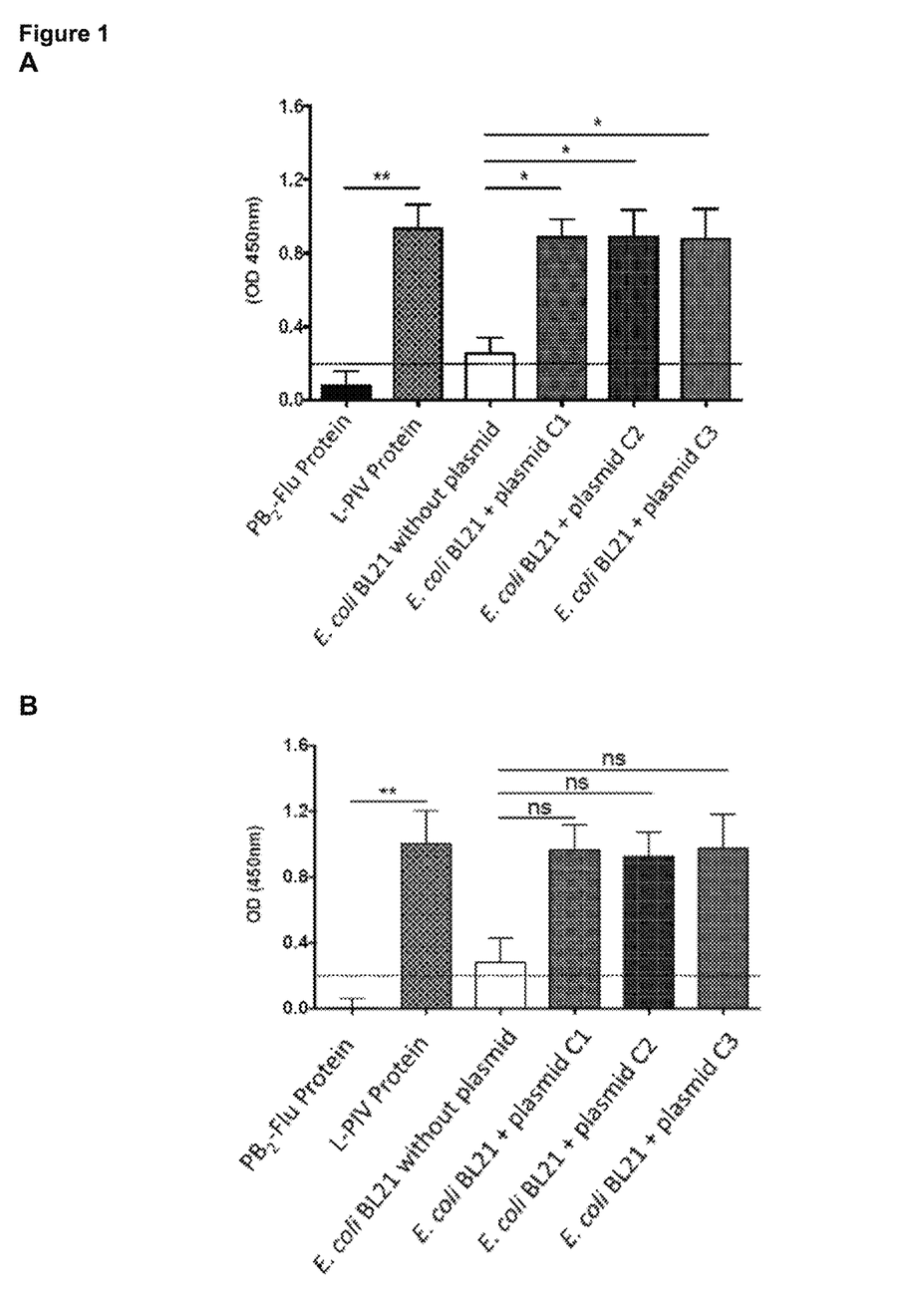

Example 3: PIV Antigen Detection Assay, Specificity Determination of PIV Anti-Monoclonal Antibodies L for Purified Antigens of PIV by Indirect ELISA Assay This assay aims to demonstrate the specificity for PIV protein L of antibodies produced by 2E11B5 and 4D8C6 hybridomas. Antigen detection was carried out using indirect ELISA technique, where ELISA plate was activated with 50 ng of purified antigen for 1 hour at 37° C. (98.6° F.). In the same way, the plate was activated with 20 µg of bacterial lysate from *E. coli* BL21 strain with no plasmid (used as specificity control) and 3 clones (C1, C2 and C3) of the same strain, in which protein L was overexpressed. Another negative control included was 50 ng of PB2 protein from Flu in a separate well. Subsequently, the plate was washed twice with 1×/Tween20 0.05% phosphate buffered saline (PBS). The plate was then blocked for 2 hours at 37° C. (98.6° F.) with 1×PBS/10% Fetal Bovine Serum (FBS). Subsequently, the washes were repeated and then each antibody (2E11B5 and 4D8C6) were incubated at a final concentration of 3.4 µg/mL (170 ng per well), diluted in 1×PBS/10% FBS, for 1 hour at 37° C. (98.6° F.) (each antibody on a separate plate). After incubation time, the washes were repeated and a secondary anti-mouse IgG antibody labeled with horseradish peroxidase (HRP) in dilution 1 in 2000 (0.5 ng/µl per well) was added to each well in 1×PBS/10% FBS, for 1 hour at room temperature (≈25° C. (77° F.)), in the dark. Finally, the washes were carried out and it was developed with 50 µL of citrate/ Tetramethylbenzidine (TMB, 3-3'-5-5'-tetramethylbenzidine, 1 mg/mL, Becton Dickinson) buffer. To stop the reaction, 50 µL of $H_2SO_4$ 2 N were added and the result was read on an ELISA reader, at 450 nm. To determine that the reaction of the secondary antibody was specific in recognizing the primary antibody and also that the obtained signal was not caused by nonspecific binding of the secondary antibody to the viral antigen, controls were carried out in which only the secondary antibody was used with no primary antibody or sample (well not activated). Another control to determine that the primary antibody reaction is specific for the antigen, consisted of using the antibodies on an ELISA plate that has not been activated with the antigen (with no antigen) or using the antibodies on an ELISA plate that possessed 50 ng of PB2 protein from Flu or *E. coli* BL21 strain lysate with no plasmid. Results show that monoclonal antibodies of the invention are capable of recognizing 50 ng of purified antigen, specifically, since they do not recognize PB2 protein of Flu, nor bacterial lysate proteins with high signal (FIGS. 1A and 1B), as observed in the case of the 3 clones that overexpress protein L. Commercial antibody was not used to compare, since there are no commercial Parainfluenza anti-L antibodies, the vast majority commercialized have been made and against phosphoprotein (P), nucleoprotein (NP) or Hemagglutinin-Neuraminidase (HN). A study was found, from Machiko Nishio et al. (2000 and 2011), in which Parainfluenza anti-L antibodies were generated. These antibodies are only directed against a PIV serotype, serotype 2 and not for the 3 most prevalent serotypes in respiratory diseases (PIV 1, 2 and 3), as is the case with these antibodies. On the other hand, published anti-L antibodies have not been commercialized so far. All negative controls used gave expected results (data not shown in the figures).

Figure 2:
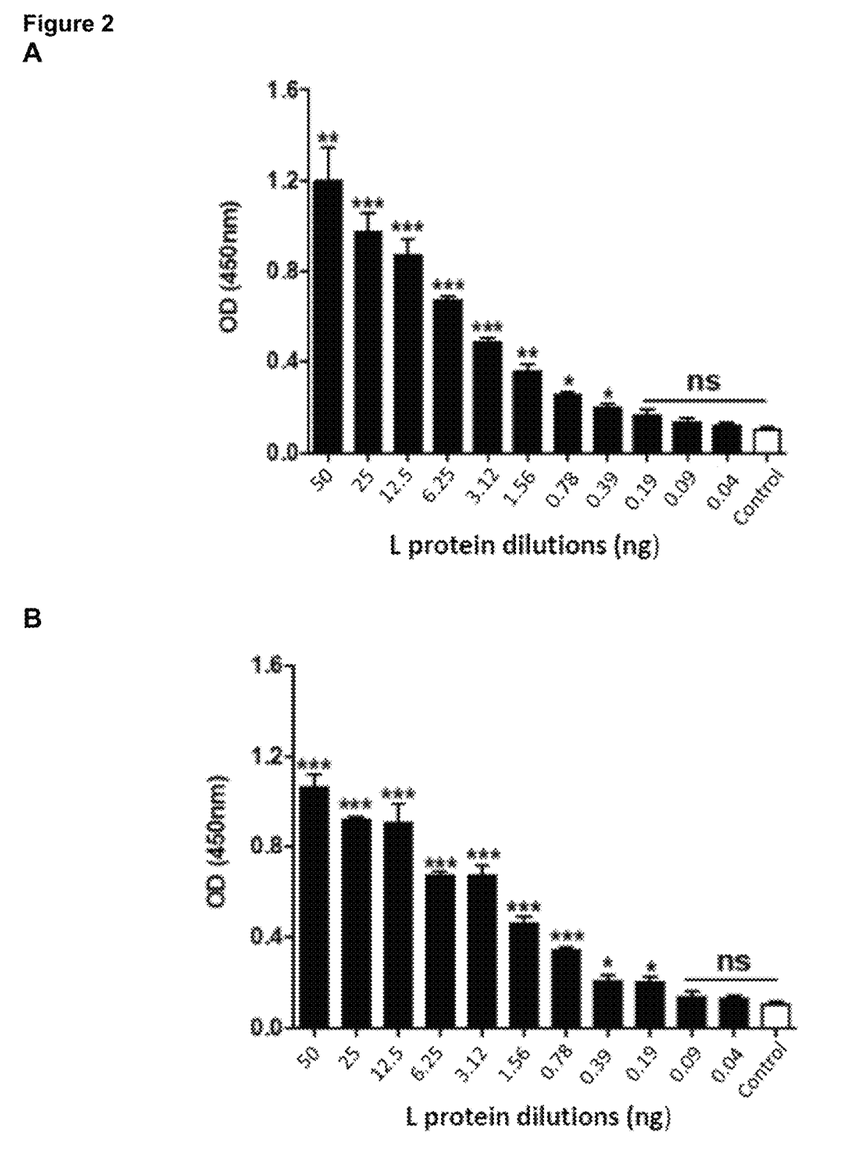

Example 4: Assay to Determine Monoclonal Antibodies Sensitivity for the Detection of PIV Anti-L Viral Antigens Assay was performed to determine the maximum protein dilution that PIV anti-monoclonal antibodies L from 2E11B5 and 4D8C6 hybridomas are able to detect by indirect ELISA. For this, the same technique described in example 3 was used. The plate was activated with 11 serial dilutions of PIV protein L 1:2, starting with 50 ng of purified antigen. Anti-L 2E11B5 and 4D8C6 antibodies were used in a final concentration of 3.4 µg/mL (170 ng/well), and were diluted in 1×PBS/10% FBS. Subsequently, anti-mouse IgG detection antibody was added in a dilution of 1:2,000 (0.5 ng/µL per well) and incubated for 1 hour at room temperature (≈25° C. (77° F.)), in the dark. Finally, the washes were carried out and it was developed with 50 µL of citrate/ Tetramethylbenzidine (TMB, 3-3'-5-5'-tetramethylbenzidine, 1 mg/mL, Becton Dickinson) buffer. To stop the reaction, 50 µL of $H_2SO_4$ 2 N were added and the result was read on an ELISA reader, at 450 nm. Results showed that the anti-L 2E11B5 antibody is capable of detecting up to 390 picograms (pg) of the PIV recombinant chimera protein L (FIG. 2A).

Anti-L antibody from 4D8C6 hybridoma showed greater sensitivity than the anti-L antibody 2E11B5 (FIG. 2B), as it was able to detect up to 190 picograms of pure protein. Controls were included in all the tests which allowed to rule out non-specific reactions of both the antibodies, which contained all components of the test except the sample (PIV protein L, data not shown in the graphs).

Figure 3:
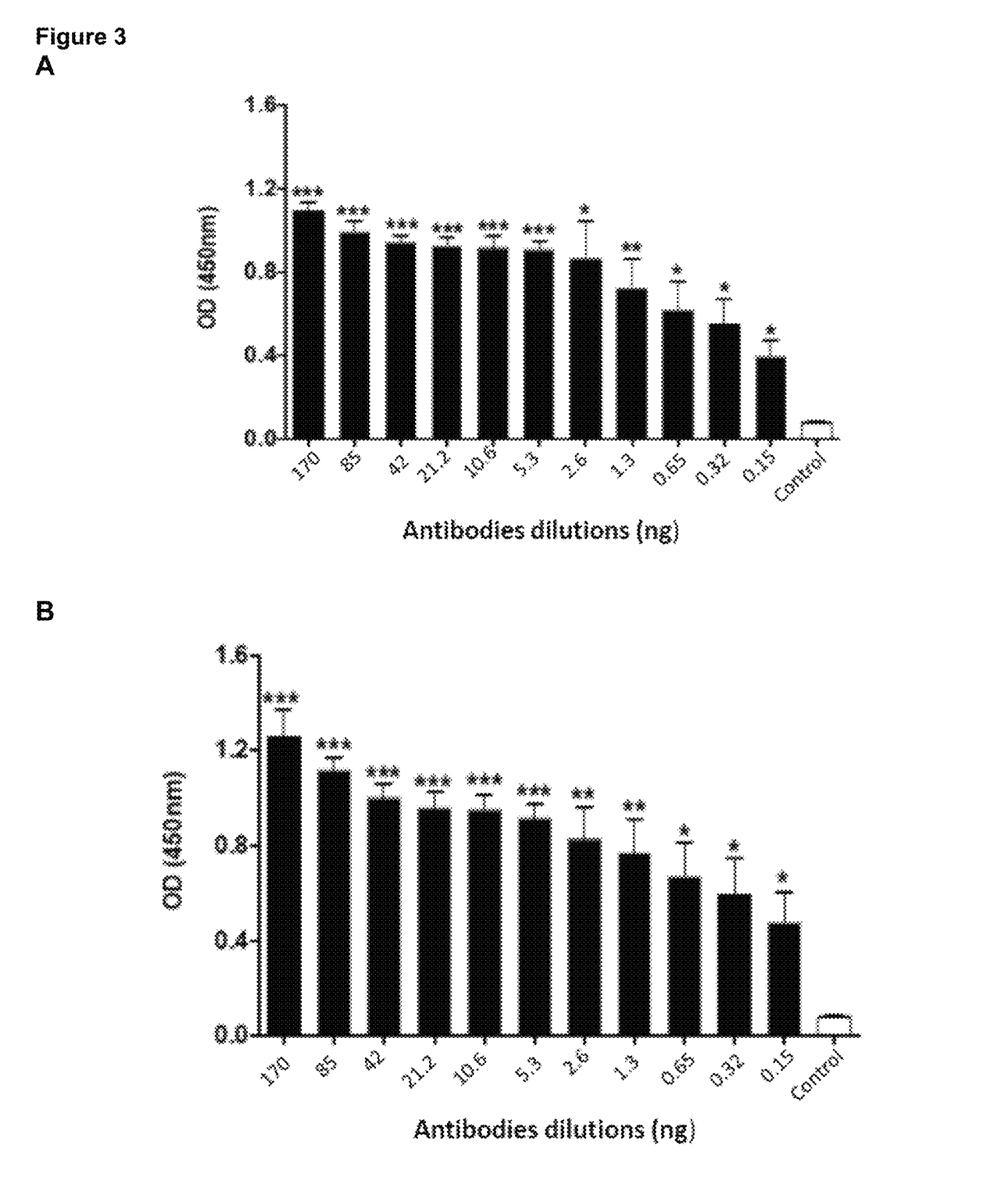
FIG. 3: Assay of serial dilutions of anti-Flu L monoclonal antibodies produced by 2E11B5 and 4D8C6 hybridomas, for the detection of purified PIV antigens. ELISA plates were activated with 50 ng of PIV recombinant protein L and antigen was detected with 11 serial dilutions of anti-2E11B5 L antibodies (A) or 4D8C6 (B) 1:2, starting from a concentration of 3.4 µg/mL (170 ng per well). Values are expressed as standard deviation average +/− of the value of absorbance emitted at 450 nm of each duplicate sample, in at least two independent experiments. *P<0.05; P<0.01 and *P<0.001 by parametric student test comparing the results of well called control (with no 2E11B5 or 4D8C6 antibody) versus each of the dilutions of antibodies.

Example 5: Assay to Determine Monoclonal Antibodies Efficiency to Detect PIV Viral Antigens, by Indirect ELISA Assay was performed to determine the maximum dilution of PIV anti-monoclonal antibodies L from 2E11B5 and 4D8C6 hybridomas which allow the detection of the viral antigen. An ELISA plate was activated with 50 ng of purified antigen (protein L) and then the plate was blocked for 2 hours at 37° C. (98.6° F.) with 1×PBS/10% Fetal Bovine Serum (FBS). Anti-L 2E11B5 and 4D8C6 antibodies were used in 1:2 dilutions, starting from the working concentration (170 ng) up to dilution 11 (0.15 ng) in 1×PBS/10% FBS. Subsequently, anti-mouse IgG detection antibody was added in a dilution of 1:2,000 (0.5 ng/μL per well) incubated for 1 hour at room temperature (≈25° C. (77° F.)), in the dark. Finally, the washes were carried out and it was developed with 50 μL of citrate/Tetramethylbenzidine (TMB, 3-3'-5-5'-tetramethylbenzidine, 1 mg/mL, Becton Dickinson) buffer. To stop the reaction, 50 μL of $H_2SO_4$ 2 N were added and the result was read on an ELISA reader, at 450 nm. In FIG. 3 (A and B) is observed that both anti-L antibodies (2E11B5 and 4D8C6) can detect 50 ng of the purified antigen with high efficiency, since detection of the antigen with high signal was observed in dilutions made. Negative control included in this assay corresponds to a well which does not contain sample (protein L), was blocked with 1×PBS/10% FBS, primary antibody (anti-L 2E11B5 or anti-L 4D8C6) was added and also contains HRP-conjugated anti-mouse IgG antibody.

Figure 4:
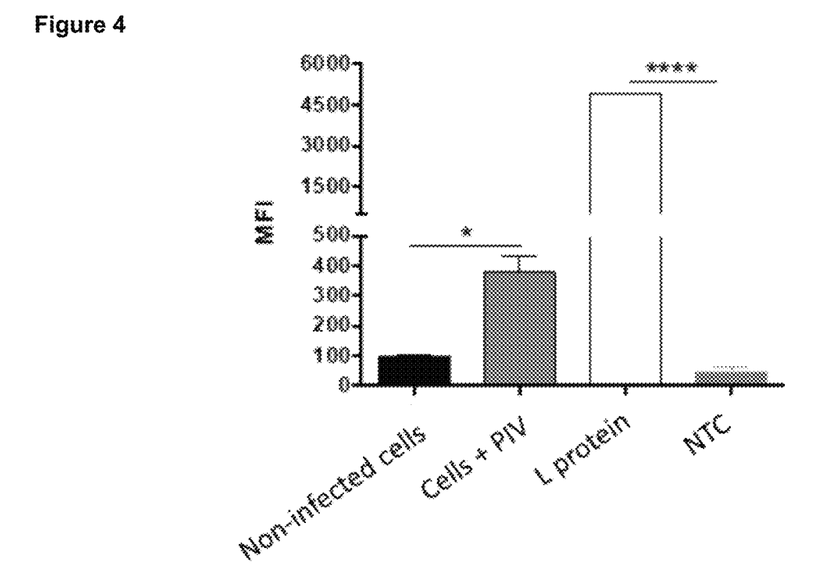

Example 6: Detection of PIV Protein L in PIV-Infected Cells, Using PIV Anti-L Monoclonal Antibodies, by Means of Luminex Sandwich Technique As in patient samples, the availability and concentration of viral proteins is generally very low in infected cells, so we wanted to evaluate the detection of the antigen of interest in PIV-infected cells (FIG. 4). For this assay, a Sandiwch-type luminex assay was performed, using anti-L 2E11B5 antibody as capture antibody and anti-L 4D8C6 as detection antibody. PIV anti-L 4D8C6 detection antibody was conjugated to the fluorosphor biotin. Luminex plates were activated with 50 magnetic microspheres per (internally labeled with red or near infrared fluorophore of different intensities) per μL, which were conjugated with the antibody secreted by 2E11B5 hybridoma (anti-PIV), functioning as a capture antibody (at a final concentration of 2.5 μM). Conjugated microspheres were incubated with 50 μL of MDCK cells PIV uninfected and infected, for 2 hours at room temperature (☐23° C. (☐73.4° F.)), stirring at 400 rpm and in the dark (covered with aluminum foil). As a negative control, no sample was incubated in a well and 50 ng of protein L was used as a positive control. After 2 hours, it was perform 2 washes with 100 μL 1×-Tween20 PBS 0.05% for 30 seconds using the manual magnetic scrubber. For detection of protein captured by 2E11B5 antibody, antibodies produced by 4D8C6 hybridoma, conjugated to biotin fluorophore, were used at a concentration of 4 μg/mL diluted in 1×PBS-1% BSA, the wells being incubated with 50 μL. Incubation is carried out for 1 hour at room temperature, in the dark, stirring at 400 rpm. 2 washes are carried out again with 100 μL 1×-Tween20 PBS 0.05% for 30 seconds using the manual magnetic scrubber. The complex formed by conjugated microspheres with capture antibody plus antigen and detection antibody is incubated with 50 μL of Streptavidin/Phycoerythrin at a final concentration of 6 μg/mL. Incubation is carried out for 30 minutes at room temperature, in the dark, stirring at 400 rpm. Finally, two more washing steps are carried out and the wells are incubated with 100 μL of Sheet fluid reagent (reagent used by Luminex equipment for the equipment to read the samples), stir 5 minutes at 400 rpm, in the dark. Results of the mean fluorescence intensity (MFI) are then read on the Luminex 200 equipment, which, through a red laser (621 nm), detects the recognition region of the microsphere and the Green laser (511 nm) detects the binding of the detection antibody to the analyte.

Obtained results for this test are shown in FIG. 4, where it can be seen that the Luminex technique, using the antibody (anti-L) from 2E11B5 hybridoma, as a capture antibody and the antibody from 4D8C6-HRP hybridoma as a detection antibody, allows the antigen to be detected in PIV-infected cells (FIG. 4), without nonspecifically detecting antigens from uninfected cells, that is, the antibodies are capable of discriminating between infected and uninfected samples. All infected cell samples detected as positive by Luminex are those that show an MFI above two standard deviations from the mean MFI of uninfected cells. Infected and uninfected cells were processed the same as clinical samples shown in Example 7.

Example 7: Clinical Diagnosis of Samples from PIV-Infected Patients, Using PIV Anti-L Monoclonal Antibodies, Using the ELISA Sandwich Technique Availability and concentration of viral proteins is generally very low in clinical samples of nasopharyngeal swabs, so it was necessary to modify the indirect ELISA assay that was previously performed. For this assay, an ELISA Sandwich was performed, using anti-L 2E11B5 antibody as capture antibody and anti-L 4D8C6 as detection antibody. PIV anti-L 4D8C6 detection antibody was conjugated to the HRP. Wells of an ELISA plate were activated with 3.4 μg/mL (170 ng/well) of anti-L antibody from PIV 2E11B5 hybridoma, diluted in 1×PBS, for 1 hour at 37° C. (98.6° F.). 2 washes were carried out with 1×-Tween20 PBS 0.05% and later the plate was blocked with 200 μL of 1×PBS/10% FBS for 1 hour at 37° C. (98.6° F.). Washed again and incubated for 1 hour at 37° C. (98.6° F.) each well with 50 μL of nasopharyngeal swabs from patients positive for PIV according to the diagnostic method "$D^3$ Ultra DFA Respiratory Virus Screening and ID Kit de DHI (Diagnostics Hibryds) USA", routinely referred to as "viral panel", and which were treated as described later. As controls were included: 1) specificity control: 50 μL of sample of patients diagnosed with Flu were used by the viral panel for anti-PIV antibodies; 2) positive control: 50 ng of recombinant L-PIV protein; 3) Negative control: corresponding to healthy control samples. Subsequently, the 2 corresponding washes were carried out with 1×-Tween20 PBS 0.05% and each well was incubated for 1 hour at room temperature (≈25° C. (≈77° F.), in the dark) with 50 μl of anti-L antibody from 4D8C6 hybridoma, conjugated with HRP (1.8 ng/μL of final concentration). The plate was then washed 2 more times, developed with 50 μL of TMB solution and incubated for 15 minutes in the dark. The reaction stopped with 50 μL of $H2SO_4$ 2 N and the plate was read at 450 nm in an ELISA reader (Epoch model), certified for clinical diagnosis.

Figure 5:
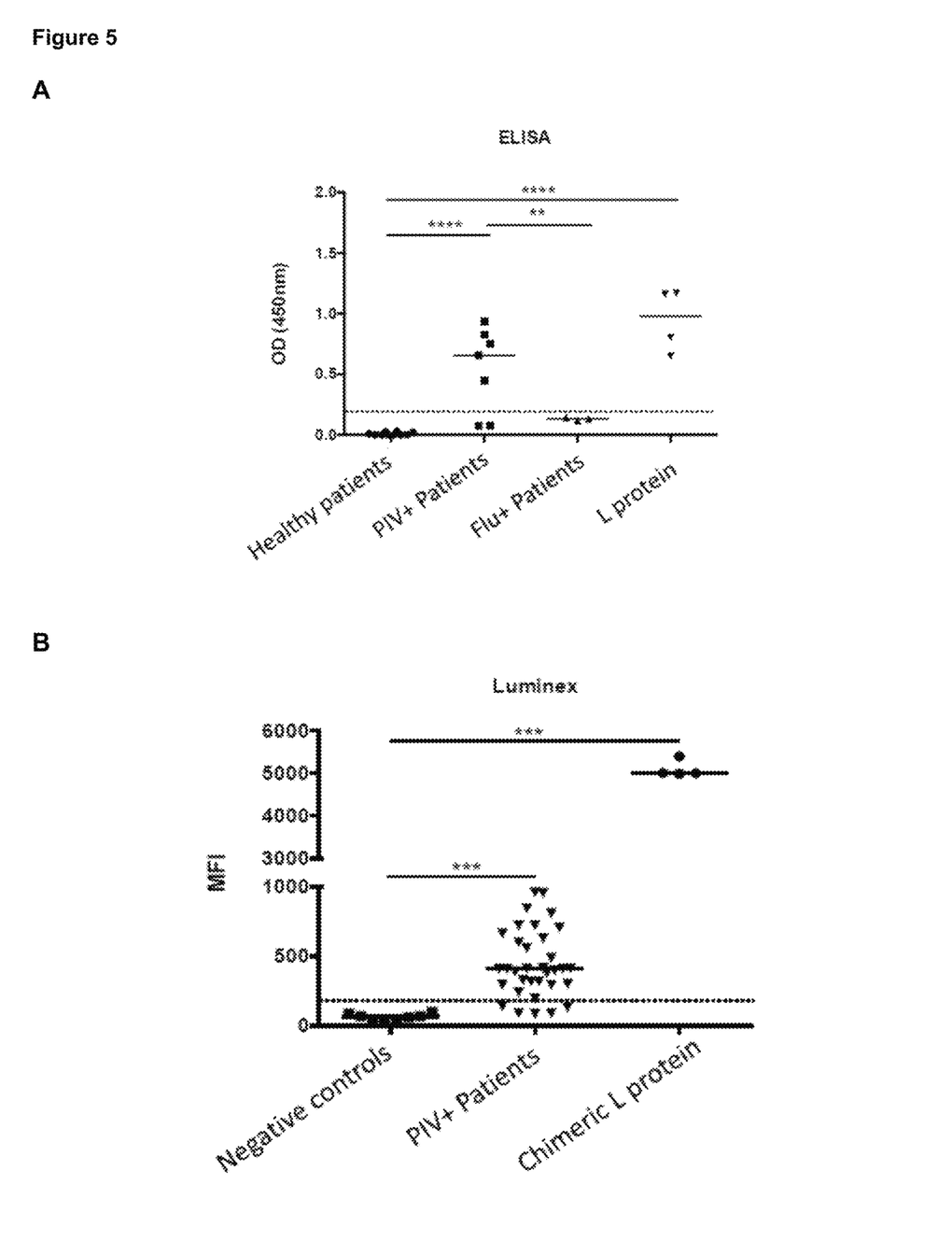

Obtained results for this test are shown in FIG. 5A, where it can be observed that the ELISA Sandwich technique using the antibody (anti-L) from 2E11B5 hybridoma, as capture antibody and the antibody from the 4D8C6-HRP hybridoma as detection antibody, allows the detection of the antigen in samples of PIV-infected patients (FIG. 5A), which were previously confirmed by direct immunofluorescence in a certified clinical laboratory using the viral panel. FIG. 5A, shows the obtained results with PIV anti-L antibodies, where 43 samples from patients diagnosed as positive PIV were used and as a specificity control, 3 samples from patients positive for the Influenza virus were included. As a positive control, wells were included to which purified L-PIV protein was added. As negative control, 10 healthy controls were analyzed. Results show that anti-PIV antibodies are specific in detecting only PIV-positive patients and not healthy controls or those infected with another virus (Flu). All samples detected positive by ELISA are those that show an optical density (OD) above 0.1.

Treatment of clinical samples. The samples used for the tests were obtained from nasopharyngeal swabs contained in universal transport medium (UTM). The samples were centrifuged at 14,000 rpm for 4 minutes at room temperature. Subsequently, the supernatant (SN1) was separated from the pellet; the latter was incubated with 100 µL of RIPA Buffer (50 mM Tris-HCl pH 8.0, 150 mM NaCl, 1% NP-40, 0.5% Sodium Deoxycholate, 0.1%, SDS and a 1× protease inhibitor cocktail) for 15 minutes at 4° C. (39.2° F.), vortexing every 5 minutes. It was then centrifuged at 14,000 rpm for 4 minutes at room temperature. At the end, the supernatant obtained (SN2) was taken and mixed with SN1, vortexing was performed.

Example 8: Clinical Diagnosis of Samples from PIV-Infected Patients, Using PIV Anti-L Monoclonal Antibodies, by Luminex Sandwich-Type As in ELISA technique, the availability and concentration of viral proteins is generally very low in clinical samples of nasopharyngeal swabs, so it was wanted to evaluate the obtained results by ELISA technique to another more sensitive technique (FIG. 5A). For this assay, a Sandwich-type luminex assay was performed, using anti-L 2E11B5 antibody as capture antibody and anti-L 4D8C6 as detection antibody. PIV anti-L 4D8C6 detection antibody was conjugated to the fluorosphor biotin. Luminex plates were activated with 50 magnetic microspheres per (internally labeled with red or near infrared fluorophore of different intensities) per µL, which were conjugated with the antibody secreted by 2E11B5 hybridoma (anti-PIV), functioning as a capture antibody (at a final concentration of 2.5 µM). Conjugated microspheres were incubated with 50 µL of nasopharyngeal swab (NPS) samples from patients with viral respiratory symptoms, for 2 hours at room temperature (23° C. (73.4° F.)), stirring at 400 rpm and in the dark (covered with aluminum foil). As negative controls, 8 samples of healthy controls were analyzed. 14 samples of patients positive for PIV were used (according to the diagnostic method "D³ Ultra DFA Respiratory Virus Screening and ID Kit de DHI (Diagnostics Hibryds) USA", routinely referred to as "viral panel", which were treated as the same way mentioned above, and as a positive control, wells were included to which purified L-PIV protein (50 ng) was added. After 2 hours, 2 washes are carried out again with 100 µL 1×-Tween20 PBS 0.05% for 30 seconds using the manual magnetic scrubber. For detection of protein captured by 2E11135 antibody, antibodies produced by 4D8C6 hybridoma, conjugated to biotin fluorophore, were used at a concentration of 4 µg/mL diluted in 1×PBS-1% BSA, the wells being incubated with 50 µL. Incubation is carried out for 1 hour at room temperature, in the dark, stirring at 400 rpm. 2 washes are carried out again with 100 µL 1×-Tween20 PBS 0.05% for 30 seconds using the manual magnetic scrubber. The complex formed by conjugated microspheres with capture antibody plus antigen and detection antibody is incubated with 50 µL of Streptavidin/Phycoerythrin at a final concentration of 6 µg/mL. Incubation is carried out for 30 minutes at room temperature, in the dark, stirring at 400 rpm. Finally, two more washing steps are carried out and the wells are incubated with 100 µL of Sheet fluid reagent (reagent used by Luminex equipment for the equipment to read the samples), stir 5 minutes at 400 rpm, in the dark. Results of the mean fluorescence intensity (MFI) are then read on the Luminex 200 equipment, which, through a red laser (621 nm), detects the recognition region of the microsphere and the Green laser (511 nm) detects the binding of the detection antibody to the analyte.

Obtained results for this test are shown in FIG. 5B, where it can be observed that the Luminex technique, as the obtained by ELISA technique using the antibody (anti-L) from 2E11B5 hybridoma, as capture antibody and the antibody from the 4D8C6-HRP hybridoma as detection antibody, allows the detection of the antigen in samples of PIV-infected patients (FIG. 5B) with high intensity, which were previously confirmed by direct immunofluorescence in a certified clinical laboratory using the viral panel. FIG. 5B, shows the obtained results with PIV anti-L antibodies, where 38 samples from patients diagnosed as positive PIV were used and 8 healthy control samples. Furthermore, as a positive control, wells were used to which purified L-PIV protein was added. Results show that anti-PIV antibodies are specific in detecting only PIV-positive patients and not control subjects. All samples detected as positive by Luminex are those that show an MFI above two standard deviations from the mean MFI of healthy controls.

This assay, as in ELISA assay with patient samples, demonstrates the versatility of antibodies from 2E11B5 and 4D8C6 hybridomas of PIV, since they are capable of simultaneously binding to antigen without competing for the binding site or interfere with each other and detect poor antigen availability in nasopharyngeal swab sample. The most interesting in these results is that it was possible to detect protein L, which is a chimera protein, which was constructed in the laboratory from the three conserved fragments of the three most prevalent serotypes of human PIV (1, 2 and 3).

Example 9: Blind Study for the Detection of L-PIV Antigen in Clinical Samples, Obtained from Patients with an Infection, Using Anti-PIV Monoclonal Antibodies, which are Part of the Respiratory Virus Multiple Detection Kit Previously, ELISA tests were carried out in Sandwich where the previous diagnosis of the samples to be evaluated was known. After these tests, a blind study was carried out, where about 150 nasopharyngeal swab samples were evaluated, without knowing the microbiological diagnosis. For all assays in the blinded study, ELISA's Sandwich were performed where anti-L 2E11B5 antibody was used as capture antibody and anti-L 4D8C6 antibody was used as HRP-conjugated detection antibody. Wells of an ELISA plate were activated with 3.4 µg/mL (170 ng/well) of anti-L antibody from PIV 2E11B5 hybridoma, diluted in 1×PBS, for 30 hour at 37° C. (98.6° F.). 2 washes were carried out with 1×-Tween20 PBS 0.05% and later the plate was blocked with 200 µL of 1×PBS/10% FBS for 30 minutes at 37° C. (98.6° F.). Each well with 50 µL of nasopharyngeal swabs from patients was washed again and incubated for 1 hour at 37° C. (98.6° F.), which were evaluated in parallel by the standard diagnostic method (PCR), routinely referred to as "viral panel", and which were treated as previously described in example 6. As controls were included: 1) specificity control: 50 µL of BSA protein (50 ng) were used; 2) positive control: 50 ng of L-PIV recombinant protein; 3) Negative controls: wells with no sample and wells blocked and incubated with detection antibody. Subsequently, the 2 corresponding washes were carried out with 1×-Tween20 PBS 0.05% and each well was incubated for 30 minutes at room temperature (≈25° C. (≈77° F.), in the dark) with 50 µl of anti-L antibody from 4D8C6 hybridoma, conjugated with HRP (1.8 ng/µL of final concentration). The plate was then washed 2 more times, developed with 50 µL of TMB solution and incubated for 15 minutes in the dark. The reaction stopped with 50 µL of H2SO$_4$ 2 N and the plate was read at 450 nm in an ELISA reader (Epoch model), certified for clinical diagnosis.

Results are shown in FIG. 5A, where the ability of antibodies to detect protein L in clinical samples is observed, since they were designed from a chimera protein. 5 out of 7 PIV positive patients were detected, and from these results the diagnostic accuracy of antibodies could be determined, which is shown in Table 1. The table shows the two concepts that define diagnostic accuracy, where we have specificity, that is, the ability of antibodies to diagnose negative samples as negative, without detecting false positives, and on the other hand, we have sensitivity, that is, the ability of antibodies to diagnose as positive those samples that really are, without diagnosing false negatives. Results set forth in the table show a high specificity percentage (100%) of antibodies against the standard technique (PCR) and a low sensitivity percentage (71%), which in turn is high considering that the antibodies were designed against a chimeric protein and not against the complete protein expressed by the virus, since the whole protein is not conserved.

TABLE 1

Diagnostic accuracy of anti-L-PIV antibodies

| PIV (N = 141) | Diagnosis by reference technique: PCB | | Specificity | Sensitivity |
|---|---|---|---|---|
| Diagnostic test: ELISA | True positives 5 | False positives 0 | 100% | 71% |
| | False negatives 2 | True negatives 134 | | |

Example 10: Protein L Detection by Indirect ELISA, Using Monoclonal Antibodies Secreted by Biotin-Conjugated 2E11B5 and 4D8C6 Hybridomas In this application example, is demonstrated that the specific monoclonal antibody against the PB2 protein can be detected by indirect ELISA.

For detection of protein L, ELISA plates were activated with 50 µL of protein L and BSA 50 ng. Specific sites were blocked with 10% FBS diluted in 1×PBS. 170 ng (3.4 µg/mL) of Fab fragments of antibodies secreted by 2E11B5 (anti-PIV) and 4D8C6 (anti-PIV) hybridomas, both previously biotin conjugated. Incubation of biotin-binding molecules (Streptavidin), which is HRP-conjugated (1:2,000 dilution, 75 ng per well) (FIG. 6, dark gray bar, 2E11B5 antibody and light gray bar, 4D8C6 antibody).

Example 10: PIV Antigen Detection Assay, Using F(Ab')2 Fragments of PIV Anti-L Monoclonal Antibodies by Indirect ELISA Assay The objective of this assay is to demonstrate the ability to detect fragments of anti-PIV antibodies, produced by 2E11B5 and 4D8C6 hybridomas, by the chimera protein L. Prior to indirect ELISA assay, fragmentation of IgG molecule of each anti PIV antibody was performed. Fragmentation was performed using the "Thermo Scientific™ Pierce™ F(ab')2 Fragment Preparation Kits" kit (#10381214, Thermo Scientific), which separates F(ab')2 fragment and Fc from the antibody of interest, by using the enzyme pepsin that digests the Fc fragment and subsequently purification steps are carried out to separate the F(ab')2 fragment from the digested Fc fragment. After antibody fragmentation, purified F(ab')2 fraction was verified by the SDS-PAGE stained technique with coomassie blue. F(ab')2 fractions were conjugated to biotin molecules using the rapid conjugation kit, Lightning-Link rapid biotin type A (#370-0010, Expedeon). Having ready all reagents, antigen detection was carried out by indirect ELISA technique, where ELISA plate was activated with 50 ng of purified L antigen for 1 hour at 37° C. (98.6° F.). Two negative controls were included, one with no sample and the other incubating the well with 50 ng of BSA protein. Subsequently, the plate was washed twice with 1×/Tween20 0.05% phosphate buffered saline (PBS). The plate was then blocked for 2 hours at 37° C. (98.6° F.) with 1×PBS/10% Fetal Bovine Serum (FBS). Subsequently, the washes were repeated and then each antibody conjugated with biotin, unfractionated and F(ab')2 fractions (2E11B5 and 4D8C6) was incubated at a final concentration of 3.4 µg/mL (170 ng per well), diluted in 1×PBS/10% FBS, for 1 hour at 37° C. (98.6° F.) (each antibody on a separate plate). After incubation time, washings were repeated and a biotin-binding protein (Streptavidin) labeled with horseradish peroxidase (HRP) enzyme was added to each well in dilution 1 in 2000 (25 ng/µL per well) in 1×PBS/10% FBS, for 1 hour at room temperature (25° C. (77° F.), in the dark. Finally, the washes were carried out and it was developed with 50 µL of citrate/Tetramethylbenzidine (TMB, 3-3'-5-5'-tetramethylbenzidine, 1 mg/mL, Becton Dickinson) buffer. To stop the reaction, 50 µL of H$_2$SO$_4$ 2 N were added and the result was read on an ELISA reader, at 450 nm. To determine that the reaction of the secondary antibody was specific in recognizing the primary antibody and also that the obtained signal was not caused by nonspecific binding of the secondary antibody to the antigen, controls were carried out in which only the secondary antibody was used with no primary antibody or sample (well not activated). Another control to determine that the primary antibody reaction is specific for the antigen, consisted of using the antibodies on an ELISA plate that has not been activated with the antigen (with no sample) or using the antibodies on an ELISA plate that possessed 50 ng of PB2.

Figure 6:
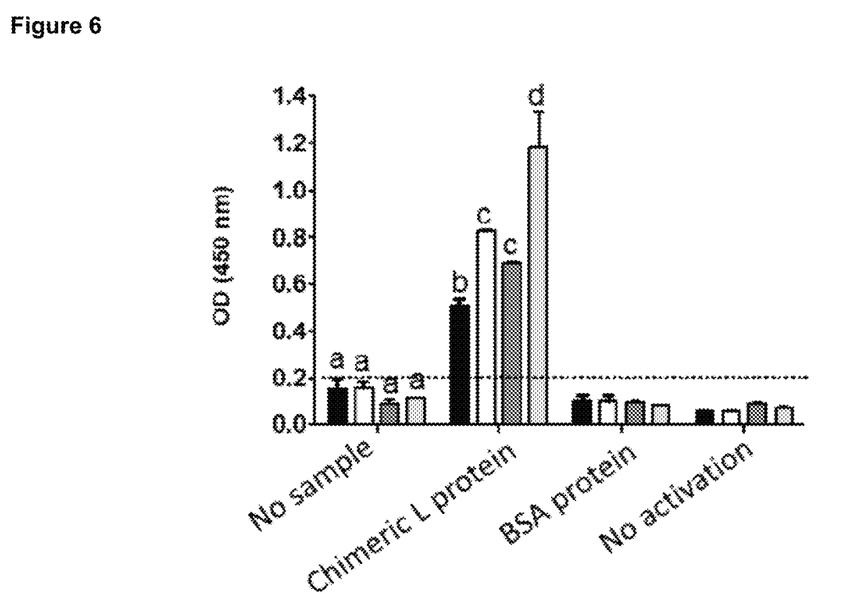
FIG. 6: protein L detection by indirect ELISA, using monoclonal antibodies secreted by biotin-conjugated 2E11B5 and 4D8C6 hybridomas. The Figure shows a graph where absorbance at 450 nm emitted by the conversion of substrate Tetramethylbenzidine to a colored compound catalyzed by the Horseradish peroxidase (HRP) enzyme is expressed. Black and white samples correspond to the assay performed with secreted antibody fragments by 2E11B5 and 4D8C6 hybridomas respectively, while in gray the assays performed with the complete monoclonal antibodies secreted by 2E11B5 and 4D8C6 hybridomas are shown. Average value of emitted absorbance at 450 nm of each sample is shown (where b is equal to p<0.0001 compared to a and d is equal to p<0.0001 compared to c; by means of the 2-way ANOVA test comparing the well with no sample versus well with protein with all antibodies).

Results show that monoclonal antibodies of the invention are capable of recognizing 50 ng of purified antigen, specifically, regardless of whether the complete antibody or a fragment thereof is used (FIG. 6, black bar, 2E11B5 antibody and white bar, 4D8C6 antibody).

The invention claimed is:

1. A monoclonal antibody or an antigen-binding portion thereof that binds to human parainfluenza virus (human PIV) protein L for use in detecting the presence and/or localization of the protein, comprising:

a light chain variable region where its CDR1 ($CDR_{LC1}$) is defined according to SEQ ID NO: 1, its CDR2 ($CDR_{LC2}$) is defined by SEQ ID NO: 2 and its CDR3 ($CDR_{LC3}$) corresponds to SEQ ID NO: 3, and a heavy chain variable region where its CDR1 ($CDR_{HC1}$) is defined according to SEQ ID NO: 4, its CDR2 ($CDR_{HC2}$) is defined by SEQ ID NO: 5 and its CDR3 ($CDR_{HC3}$) corresponds to Gly Ala Tyr, or a light chain variable region where its CDR1 ($CDR_{LC1}$) is defined according to SEQ ID NO: 6, its CDR2 ($CDR_{LC2}$) is defined by SEQ ID NO: 7 and its CDR3 ($CDR_{LC3}$) corresponds to SEQ ID NO: 8, and a heavy chain variable region where its CDR1 ($CDR_{HC1}$) is defined according to SEQ ID NO: 9, its CDR2 ($CDR_{HC2}$) corresponds to SEQ ID NO: 10 and its CDR3 ($CDR_{HC3}$) corresponds to Gly Ala Tyr, wherein said antibody can be used as detection or capture antibody.

2. A method to detect human PIV virus in a biological sample comprising contacting the biological sample with the monoclonal antibody or an antigen-binding portion thereof that binds to human PIV chimeric protein L according to claim 1 and detecting the binding of the antibody to antigen, thereby detecting the human PIV virus in the sample.

3. The method to detect human PIV virus in a biological sample of claim 2, wherein the biological sample is selected from the group consisting of in vitro cells infected with human PIV, nasal secretions, nasal washes, cerebrospinal fluid, pharyngeal secretions and bronchial washes or secretions.

4. The method to detect human PIV virus in a biological sample according to claim 2 wherein the assay used to detect the binding of the antibody to antigen is selected from: ELISA, immunofluorescence, immunohistochemistry, immunochromatography, flow cytometry, cell sorter, immunoprecipitation and Western blot.

5. The method to detect human PIV virus in a biological sample according to claim 2, wherein the antibody or an antigen-binding portion thereof is conjugated with a marker that allows its detection.

6. The method to detect human PIV virus in a biological sample according to claim 5, wherein the antibody is conjugated to a marker selected from the group consisting of fluorophores, biotin, radioisotopes, metals and enzymes.

7. A kit for detection of human PIV virus comprising:

a monoclonal antibody or an antigen-binding portion thereof that binds to human PIV chimeric protein L according to claim 1, which acts as a capture or detection antibody, wherein detection antibody is conjugated to a marker for its detection;

a solid support to which the capture antibody is attached; and reagents for detecting the marker that is conjugated to the detection antibody, wherein the marker is selected from the group consisting of fluorophores, biotin, radioisotopes, metals, and enzymes.

8. The kit for detection of human PIV viruses of claim 7, wherein the solid support is a membrane formed by one of the compounds selected from the group consisting of nitrocellulose, cellulose, polyethylene and nylon.

9. The kit for qualitative and/or quantitative detection of human PIV virus according to claim 7, wherein the detection of human PIV is carried out with an immunochromatographic test, Luminex assay, flow cytometry, immunofluorescence, radioimmunoassay, Western blot, Dot blot, ELISA, immunodiffusion or immunoprecipitation.

* * * * *

SEQUENCE LISTING

<160> NUMBER OF SEQ ID NOS: 10

<210> SEQ ID NO 1

```
<211> LENGTH: 15
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      1

<400> SEQUENCE: 1

Lys Ser Ser Gln Ser Leu Leu Asp Ser Asp Gly Lys Thr Leu Asn
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      2

<400> SEQUENCE: 2

Leu Val Ser Lys Leu Asp Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      3

<400> SEQUENCE: 3

Trp Gln Ser Thr His Phe Pro Gln Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic - Hybridoma 2E1B5 - Anti L PIV CDRHC
      1

<400> SEQUENCE: 4

Gly Tyr Tyr Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic - Hybridoma 2E1B5 - Anti L PIV CDRHC
      2

<400> SEQUENCE: 5

Arg Ile Asn Pro Tyr Asn Gly Ala Thr Arg Tyr Asn Gln Asn Phe Lys
1               5                   10                  15

Asp

<210> SEQ ID NO 6
<211> LENGTH: 15
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      1
```

```
<400> SEQUENCE: 6

Lys Ser Ser Gln Ser Leu Leu Asp Ser Asp Gly Lys Thr Leu Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      2

<400> SEQUENCE: 7

Leu Val Ser Lys Leu Asp Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic - Hybridoma 2E1B5 - Anti L PIV CDRLC
      3

<400> SEQUENCE: 8

Trp Gln Ser Thr His Phe Pro Gln Thr
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic - Hybridoma 2E1B5 - Anti L PIV CDRHC
      1

<400> SEQUENCE: 9

Gly Tyr Tyr Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic - Hybridoma 2E1B5 - Anti L PIV CDRHC
      2

<400> SEQUENCE: 10

Arg Ile Asn Pro Tyr Asn Gly Ala Thr Ser Tyr Asn Gln Asn Phe Lys
1               5                   10                  15
Asp
```